United States Patent [19]

Muro et al.

[11] Patent Number: 5,389,625

[45] Date of Patent: Feb. 14, 1995

[54] CEPHALOSPORIN COMPOUNDS

[75] Inventors: Hiroyuki Muro, Shiga; Masayasu Kasai, Kyoto; Satoru Hatano, Kameoka; Ken-ichi Nishimura; Susumu Nishizawa, both of Kyoto; Nobuharu Kakeya, Nagaokakyo, all of Japan

[73] Assignee: Kyoto Pharmaceutical Industries, Ltd., Kyoto, Japan

[21] Appl. No.: 849,019

[22] PCT Filed: Oct. 24, 1990

[86] PCT No.: PCT/JP90/01370

§ 371 Date: Jun. 8, 1992

§ 102(e) Date: Jun. 8, 1992

[87] PCT Pub. No.: WO91/06549

PCT Pub. Date: May 16, 1991

[30] Foreign Application Priority Data

Oct. 28, 1989 [JP] Japan .................................. 1-280397

[51] Int. Cl.$^6$ .................. C07D 501/22; A61K 31/545
[52] U.S. Cl. ..................................... 514/202; 540/222
[58] Field of Search .................. 540/222, 221; 514/202

[56] References Cited

U.S. PATENT DOCUMENTS 4,477,447  10/1984  Ueda et al. .......................... 424/246

FOREIGN PATENT DOCUMENTS 0054512  12/1981  European Pat. Off. .
0060422   2/1982  European Pat. Off. .
0065745   5/1982  European Pat. Off. .
2111043   6/1983  United Kingdom .

*Primary Examiner*—Nicholas Rizzo
*Attorney, Agent, or Firm*—Leydig, Voit & Mayer, Ltd.

[57] ABSTRACT

Cephalosporin compounds of the formula (I)

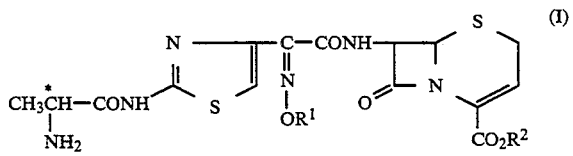

wherein $R^1$ is hydrogen atom or lower alkyl, and $R^2$ is 1-alkanoyloxyalkyl or 1-alkoxycarbonyloxyalkyl, their pharmaceutically acceptable salts, methods for producing them, and pharmaceutical use thereof.

The cephalosporin compounds and their salts are superior in absorption from digestive tract, and upon absorption from the digestive tract, show a wide range of antimicrobial activities in the body as hydrolysis products, and in addition, they have 10–400 times greater sweetness than sucrose. Thus, said compounds are useful as agents to be administered orally for the prophylaxis and treatment of bacterial infectious diseases.

10 Claims, No Drawings

CEPHALOSPORIN COMPOUNDS

TECHNICAL FIELD

The present invention relates to novel cephalosporin compounds which are useful for the prophylaxis and treatment of bacterial infectious diseases and are noticeably sweet, and to methods for producing same. More specifically, the present invention relates to cephalosporin compounds which are excellent in absorption from the digestive tract, show a wide range of antimicrobial activities in the body after being absorbed from the digestive tract, and have 10-400 times greater sweetness than sucrose, to their pharmaceutically acceptable salts, and to methods for producing them.

BACKGROUND ART

In general, cephalosporin compounds are poor in absorption from digestive tract, and therefore, are usually administered by injection. For example, there have been known cephalosporin compounds which have a wide range of excellent antimicrobial activities and are represented by the following formula (A)

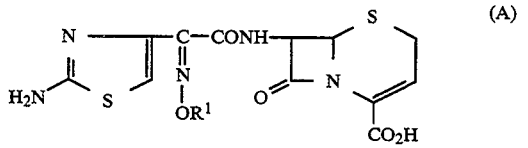

wherein $R^1$ is hydrogen atom or lower alkyl, and salts thereof [hereinafter the compounds encompassed in formula (A) including known compounds are referred to as Compound (A)]. However, said Compound (A) is also poor in absorption from digestive tract, rendering administration by injections inevitable.

Although various attempts to introduce a liposoluble ester residue into the 4-position carboxylic acid of Compound (A) to improve absorption from the digestive tract, and to produce compounds capable of converting into Compound (A) by decomposition upon absorption into blood are currently in progress, such compounds are all unsatisfactory since they permit no improvement in absorption from the digestive tract and show inconsistent absorption due to their poor solubility in water. In addition, the compounds obtained as a result of such attempts are generally poor in taste, particularly bitter, making formulation of pharmaceutical preparations easily taken very difficult.

DISCLOSURE OF THE INVENTION

The object of the present invention is to provide cephalosporin compounds having good solubility in water, easily absorbed from digestive tract, extremely good in taste (sweet), and capable of exerting excellent antimicrobial activities of Compound (A) in the body, which can be obtained by chemically modifying Compound (A).

The present inventors have conducted various investigations for the purpose of producing cephalosporin compounds, wherein the basic structure is formula (A), which allow absorption from digestive tract by oral administration, and found that the cephalosporin compounds of the following formula (I) and salts thereof are soluble in water and markedly superior in absorption from digestive tract, that upon absorption, they are converted into Compound (A) or salt thereof in blood, and high concentration of the Compound (A) or salt thereof in blood lasts for a long period, and that said compounds have extremely strong sweetness; with these findings, the present inventors further developed and completed the present invention.

That is, the present invention relates to cephalosporin compounds of the formula (I)

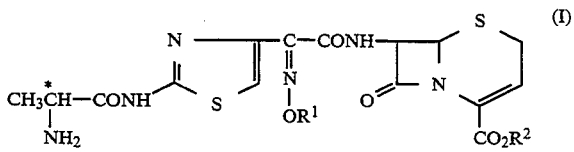

wherein $R^1$ is hydrogen atom or lower alkyl, and $R^2$ is 1-alkanoyloxyalkyl or 1-alkoxycarbonyloxyalkyl [hereinafter sometimes referred to as Compound (I)], pharmaceutically acceptable salts thereof, and methods for producing them.

In the present specification, each symbol stands for the following.

As regards $R^1$, lower alkyl may be straight- or branched-chain, and preferably exemplified by those having 1 to 4, particularly 1 to 3 carbon atoms such as methyl, ethyl, propyl, isopropyl and cyclopropyl.

As regards $R^2$, the alkanoyl moiety of 1-alkanoyloxyalkyl has 2 to 10, preferably 2 to 7 carbon atoms, and the alkyl moiety has 1 or 2 carbon atoms. Such group includes, for example, acetoxymethyl, propionyloxymethyl, iso-propionyloxymethyl, n-butyryloxymethyl, iso-butyryloxymethyl, pivaloyloxymethyl, n-valeryloxymethyl, 2-methylbutyryloxymethyl, isovaleryloxymethyl, n-hexanoyloxymethyl, 3-methylvaleryloxymethyl, neohexanoyloxymethyl, 2-methylhexanoyloxymethyl, 2,2-dimethylbutyryloxymethyl, diethylacetoxymethyl, dipropylacetoxymethyl, 2,2-dimethylvaleryloxymethyl, neoheptanoyloxymethyl, cyclohexanoyloxymethyl, cyclohexylacetoxymethyl, 1-acetoxyethyl, 1-n-propionyloxyethyl, 1-n-butyryloxyethyl, 1-isobutyryloxyethyl, 1-n-valeryloxyethyl, 1-pivaloyloxyethyl, 1-iso-valeryloxyethyl, 1-n-hexanoyloxyethyl and 1-cyclohexanoyloxyethyl.

The alkoxy moiety of alkoxycarbonyloxyalkyl represented by $R^2$ preferably has 1 to 10, more preferably 1 to 7 carbon atoms, and the alkyly moiety has 1 or 2 carbon atoms. Such group includes, for example, 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, 1-tertbutoxycarbonyloxyethyl, 1-pentyloxycarbonyloxyethyl and 1-cyclohexyloxycarbonyloxyethyl.

Preferred as $R^2$ are acetoxymethyl, propionyloxymethyl, n-butyryloxymethyl, iso-valeryloxymethyl, pivaloyloxymethyl, 1-acetoxyethyl, 1-propionyloxyethyl, 1-iso-butyryloxyethyl, 1-n-valeryloxyethyl, 1-iso-valeryloxyethyl, 1-pivaloyloxyethyl, 1-ethoxycarbonyloxyethyl, 1-iso-propoxycarbonyloxyethyl and 1-cyclohexyloxycarbonyloxyethyl.

Compound (I) forms pharmaceutically acceptable salts, preferably acid addition salts at the amino group. The acids for forming such acid addition salts are subject to no particular limitation as long as they are capable of forming salts with the amino group and are pharmaceutically acceptable, and are exemplified by mineral acids such as hydrochloric acid, sulfuric acid, phosphoric acid and nitric acid, and organic acids such as oxalic acid, fumaric acid, maleic acid, citric acid, tartaric acid, methanesulfonic acid and toluenesulfonic acid.

Compound (I) and its pharmaceutically acceptable salt are preferably syn-isomers.

Compound (I) has optically active isomers at the carbon atom marked with * in formula (I), and the present invention embraces L-compound, D-compound, and DL-compound, with preference given to L-compound.

Compound (I) and its pharmaceutically acceptable salt can be produced as in the following.

Method 1

A method wherein a compound of the formula (II)

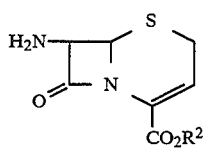

wherein $R^2$ is as defined above [hereinafter referred to as Compound (II)] is reacted with a compound of the formula (III)

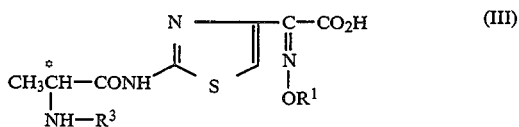

wherein $R^1$ is as defined above, and $R^3$ is hydrogen atom or amino-protecting group [hereinafter referred to as Compound (III)] or its reactive derivative.

Compound (III) is used in the instant reaction as a free carboxylic acid, or its reactive derivative, and both modes are encompassed in the present invention. Namely, Compound (III) is used in said acylation in the form of a free acid, or a reactive derivative such as a salt of sodium, potassium, calcium, triethylamine or pyridine, acid halide thereof (acid chloride, acid bromide, etc.), acid anhydride, mixed acid arthydride such as substituted phosphoric acid (e.g. dialkylphosphoric acid), alkyl carbonate (e.g. monoethyl carbonate), active amide (e.g. amide with imidazole), and ester (e.g. cyanomethyl ester, 4-nitrophenyl ester).

When using Compound (III) in the form of a free acid or a salt, the reaction is preferably conducted in the presence of a condensing agent. The condensing agent includes, for example, N,N-di-substituted carbodiimides such as N,N-dicyclohexylcarbodiimide, carbodiimide compounds such as 1-ethyl-3-(3'-dimethylaminopropyl)carbodiimide, N-cyclohexyl-N'-morpholinoethylcarbodiimide and N-cyclohexyl-N'-(4-diethylaminocyclohexyl)carbodiimide, azolide compounds such as N,N-carbonyldiimidazole and N,N-thionyldiimidazole, and reagents prepared by reacting an amide compound such as N-methylformamide and N,N-dimethylformamide and a halogen compound such as thionyl chloride, phosphorus oxychloride and phosgene, so-called Vilsmeier Reagent. When these condensing agents are used, the reaction is believed to proceed via reactive derivative of carboxylic acid.

In the present reaction, $R^3$ of formula (III) representing Compound (III) is preferably an amino-protecting group. In this case, Compound (I) is obtained in a protected form as a result of the reaction of Compound (II) and Compound (III). This protecting group can be eliminated by a method known per se.

The amino-protecting group includes phthaloyl, formyl, monochloroacetyl, dichloroacetyl, trichloroacetyl, trifluoroacetyl, methoxycarbonyl, ethoxycarbonyl, benzyloxycarbonyl, p-nitrobenzyloxycarbonyl, diphenylmethyloxycarbonyl, methoxymethylcarbonyl, methoxymethyloxycarbonyl, trimethylsilyl, 2,2,2-trichloroethoxycarbonyl, 2-methylsulfonylethyloxycarbonyl, t-butoxycarbonyl (hereinafter sometimes referred to as BOC) and trityl.

The present reaction is normally conducted in an inert solvent which is exemplified by water, organic solvents such as acetone, dioxane, acetonitrile, chloroform, benzene, methylene chloride, ethylene chloride, tetrahydrofuran, ethyl acetate, N,N-dimethylformamide and pyridine, and mixtures thereof.

The present reaction is preferably conducted at room temperature to under cooling ($-20°$ C.$-0°$ C.).

The protecting group can be eliminated in various manners according to the kind of the protecting group, such as by decomposition with acid (e.g. hydrochloric acid, trifluoroacetic acid for formyl, t-butoxycarbonyl and trityl), decomposition with base (e.g. sodium hydroxide, sodium bicarbonate for dichloroacetyl and trifluoroacetyl), decomposition with hydrazine (e.g. hydrazine for phthaloyl), and by catalytic reduction such as decomposition with palladium-carbon for benzyl and benzyloxycarbonyl, which may be conducted by methods conventionally used for the syntheses of β-lactam and peptide.

Compound (II) can be produced by esterification of a compound of the formula (II-1)

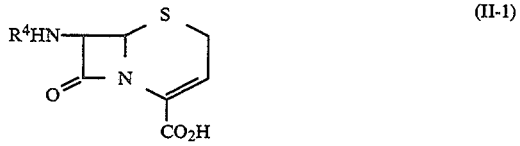

wherein $R^4$ is hydrogen atom or amino-protecting group [hereinafter referred to as Compound (II-1)], specifically by reacting Compound (II-1) with a compound of the formula (VII)

wherein $R^2$ is as defined above, and X is a group reactive with carboxyl or a group reactive with a reactive group of carboxyl [hereinafter referred to as Compound (VII)].

As regards $R^4$ of formula (II-1), the amino-protecting group includes amino-protecting groups known per se, such as benzylcarbonyl, 2-thienylacetyl, 2-furylacetyl, D-5-amino-5-carboxyvaleryl, trityl, phthalimide and o-hydroxybenzylidene.

With regard to formula (VII), the group reactive with carboxyl or a group reactive with a reactive group of carboxyl, which is represented by X includes, for example, halogen (e.g. bromine, chlorine, iodine), alkylsulfonyloxy (e.g. methanesulfonyloxy) and arylsulfonyloxy (e.g. p-toluenesulfonyloxy).

In the present reaction, Compound (II-1) is preferably subjected to the reaction after being converted into its reactive derivative such as alkali metal salt (e.g. sodium salt, potassium salt), alkaline earth metal salt (e.g. calcium salt), triethylamine salt and pyridine salt.

This reaction is easily conducted in the presence of a solvent which does not adversely affect the reaction, such as dimethylformamide, dimethylacetamide, hexamethylenephosphoric triamide, acetone and acetonitrile, normally under cooling at −20°–40° C., preferably at −20°–0° C., to avoid by-product of Δ²-isomer.

In the present reaction, R⁴ in formula (II-1) is preferably an amino-protecting group. In this case, a compound wherein the 7-position amino group of formula (II) is protected can be obtained as a result of the reaction of Compound (II-1) and Compound (VII). This protecting group can be eliminated by a method known per se.

The means for eliminating the protecting group include decomposition with methanol to be conducted following conversion into iminochloro compound by phosphorus pentachloride for benzylcarbonyl, 2-thienylacetyl, 2-furylacetyl and D-5-amin0-5-carboxyvaleryl, treating with an acid such as hydrochloric acid, formic acid and trifluoroacetic acid for trityl and o-hydroxybenzilidene, and the Ing-Manske method using hydrazine for phthalimide.

Compound (III) can be produced by reacting a compound of the formula (X)

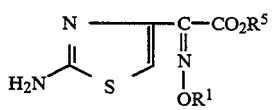
(X)

wherein R¹ is as defined above, and R⁵ is hydrogen atom or carboxyl-protecting group [hereinafter referred to as Compound (X)] with a compound of the formula (V)

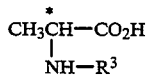
(V)

wherein R³ is as defined above [hereinafter referred to as Compound (V)], or by reacting a compound of the formula (XI)

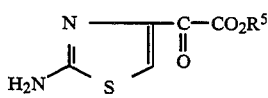
(XI)

wherein R⁵ is as defined above [hereinafter referred to as Compound (XI)] with a compound of Compound (V) to obtain a compound of the formula (XII)

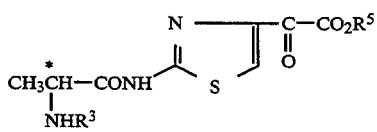
(XII)

wherein R³ and R⁵ are as defined above [hereinafter referred to as Compound (XII)], which is then reacted with a compound of the formula (IX)

(IX)

wherein R¹ is as defined above [hereinafter referred to as Compound (IX)], followed by elimination of R⁵ as necessary when R⁵ is a carboxyl-protecting group.

As regards R⁵, the carboxyl-protecting group is exemplified by, for example, methyl, ethyl, n-propyl, isopropyl, n-butyl, t-butyl, benzyl, p-nitrobenzyl, p-methoxybenzyl, benzhydryl, phenyl, p-nitrophenyl, methoxymethyl, ethoxymethyl, benzyloxymethyl, acetoxymethyl, methylthiomethyl, trityl, 2,2,2-trichloroethyl, trimethylsilyl, diphenylmethoxybenzenesulfonylmethyl and dimethylaminoethyl.

The reaction of Compound (X) or Compound (XI) and Compound (V) can be conducted in the same manner as in the reaction of Compound (IV) and Compound (V) to be described later in Method 2. In this reaction, it is preferable that the carboxyl group should be protected.

The reaction of Compound (XII) and Compound (IX) can be conducted in the same manner as in the reaction of Compound (VIII) and Compound (IX) to be described later in Method 4. The present reaction generally proceeds rapidly with a free carboxylic scid.

Method 2

A method wherein a compound of the formula (IV)

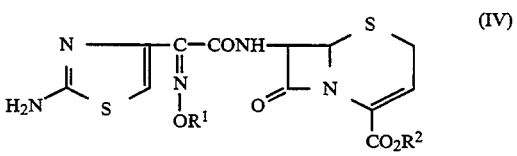
(IV)

wherein R¹ and R² are as defined above [hereinafter referred to as Compound (IV)] is reacted with Compound (V).

Compound (V) is subjected to the reaction as a free carboxylic acid or its reactive derivative, both of which modes are encompassed in the present invention. Namely, Compound (V) is subjected to acylation in the form of a free acid, or a reactive derivative such as a salt of sodium, potassium, calcium, triethylamine or pyridine, acid halide thereof (e.g. acid chloride, acid bromide, etc.), acid anhydride, mixed acid anhydride such as substituted phosphoric acid (e.g. dialkylphosphoric acid), alkyl carbonate (e.g. monaethyl carbonate), active amide (e.g. amide with imidazole), and ester (e.g. cyanomethyl ester, 4-nitrophenyl ester).

When using Compound (V) in the form of a free acid or a salt, the reaction is preferably carried out in the presence of a suitable condensing agent. The condensing agent includes, for example, N,N-di-substituted carbodiimides such as N,N-dicyclohexylcarbodiimide, carbodiimide compounds such as 1-ethyl-3-(3'-dimethylaminopropyl)carbodiimide, N-cyclohexyl-N'-morpholinoethylcsrbodiimide and N-cyclohexyl-N'-(4-diethylaminocyclohexyl)carbodiimide, azolide compounds such as N,N-carbonyldiimidazole and N,N-thionyldiimidazole, and reagents prepared by reacting an amide compound such as N-methylformamide and N,N-dimethylformamide, and a halogen compound such as thionyl chloride, phosphorus oxychloride and phosgene, so-called Viismeier Reagent. When these condensing agents are used, the reaction is believed to proceed via reactive derivative of carboxylic acid. In the present reaction, it is preferable that a base such as 4-dimethylaminopyridine should be used as a catalyst.

In the present reaction, R³ of formula (V) is preferably an amino-protecting group. In this case, Compound (I) is obtained in a protected form as a result of the reaction of Compound (IV) and Compound (V). This protecting group can be eliminated by a method known per se.

The amino-protecting group includes those mentioned above.

The present reaction is normally conducted in an inert solvent which is exemplified by water, organic solvents such as acetone, dioxane, acetonitrile, chloroform, benzene, methylene chloride, ethylene chloride, tetrahydrofuran, ethyl acetate, N,N-dimethylformamide and pyridine, and mixtures thereof.

This reaction is easily conducted in the presence of a solvent which does not adversely affect the reaction, such as dimethylformamide, dimethylacetamide, dimethyl sulfoxide, hexamethylenephosphoric trialhide, acetone and acetonitrile under cooling to avoid by-product of $\Delta^2$-isomer.

The starting compound (IV) can be prepared by reacting Compound (II) and Compound (X) in the same manner as in Method 1.

Method 3

A method wherein a compound of the formula (VI)

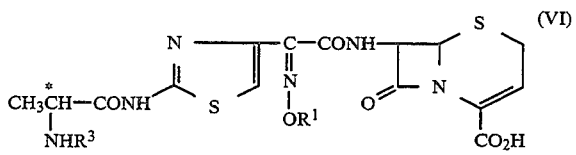

wherein $R^1$ and $R^3$ are as defined above [hereinafter referred to as Compound (VI)] is reacted with Compound (VII).

Compound (VI) is preferably subjected to the reaction in the form of a reactive derivative such as alkali metal salt (e.g. sodium salt, potassium salt), alkaline earth metal salt (e.g. calcium salt), triethylamine salt and pyridine salt.

The present reaction is easily conducted in the presence of a solvent which does not adversely affect the reaction, such as dimethylformamide, dimethylacetamide, hexamethylenephosphoric triamide, acetone and acetonitrile, normally under cooling at $-20°$–$40°$ C., preferably at $-20°$–$0°$ C. to avoid by-product of $\Delta^2$-isomer.

In the present reaction, $R^3$ of formula (VI) is preferably an amine-protecting group. In this case, Compound (I) is obtained in a protected form as a result of the reaction between Compound (VI) and Compound (VII). This protecting group can be eliminated by a method known per se.

The starting compound (VI) can be prepared by reacting Compound (II-1) and Compound (III) in the same manner as in Method 1.

Method 4

A method wherein a compound of the formula (VIII)

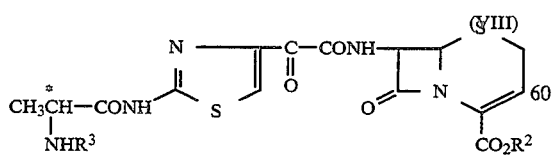

wherein $R^2$ and $R^3$ are as defined above [hereinafter referred to as Compound (VIII)] is reacted with Compound (IX).

Compounds (VIII) and (IX) are normally reacted in a solvent such as dimethylformamide, dimethylacetamide, acetonitrile, dioxane, tetrahydrofuran, alcohol, other solvents which do not adversely affect the reaction and mixtures thereof with water. The reaction normally proceeds at a temperature between room temperature and 60° C. for 30 minutes to a dozen odd hours. By removing the protecting group from the compound thus obtained as necessary by a method similar to the one mentioned above, Compound (I) can be obtained.

The starting compound (VIII) can be prepared by a method known per se, namely, by acylation of Compound (II) using Compound (XII).

Compound (I) can be converted to its pharmaceutically acceptable salt by a method known per se.

Compound (I) and pharmaceutically acceptable salt thereof obtained by the methods described above are separated from the reaction mixture by conventional methods. For example, they can be adsorbed onto adsorptive resins such as Amberlite XAD-2 (Rohm and Haas) arid Diaion HP-20 (Mitsubishi Kasei), and eluted with aqueous organic solvents, followed by purification. When necessary, chromatography using Sephadex LH-20 or G-10 (Pharmacia) may be employed.

Compound (I) and pharmaceutically acceptable salt thereof are superior in absorption from digestive tract, and upon absorption, they are hydrolyzed by enzymes in the body into Compound (A) or its pharmaceutically acceptable salt. Said Compound (A) and its salt possess excellent antimicrobial activities, and show markedly superior antimicrobial activities against Gram-positive bacteria such as *Staphylococcus aureus* and *Staphytococcus epidermidis*, and Gram-negative bacteria such as *Escherichia coli, Klebsiella pneumoniae, Proteus vutgaris, Proteus mirabittis,* and *Proteus morganii.* The Compound (A) and its salt obtained by hydrolysis of Compound (I) and its pharmaceutically acceptable salt are markedly improved in antimicrobial activities against Gram-positive bacteria, while retaining antimicrobial activities against Gram-negative bacteria, and are valuable antimicrobial agents with extremely low toxicity.

In addition, Compound (I) and its pharmaceutically acceptable salt can be swiftly absorbed into blood by oral administration, permitting high concentration of Compound (A), a metabolized compound thereof, or its pharmaceutically acceptable salt in blood, and long duration of the high concentration. By converting Compound (I) into its salt, solubility in digestive tract can be greatly enhanced, which in turn leads to improved absorption efficiency and improved absorption of Compound (I) into blood.

Another characteristic property of the present invention lies in the fact that Compound (I) and its pharmaceutically acceptable salt have noticeable sweetness which is normally 10 to 400 times greater than that of sucrose.

Compound (I) and its pharmaceutically acceptable salt are useful for the prophylaxis and treatment of bacterial infectious diseases. Said agents for the prophylaxis and treatment of bacterial infectious diseases can be used as agents for preventing and treating bacteria-caused diseases of warm-blooded animals including humans (e.g. dogs, cats, cows, horses, rats, mice), such as suppurative diseases, infectious diseases of respiratory organs, biliary infectious diseases and infectious diseases in the urinary tract.

Compound (I) and its pharmaceutically acceptable salt of the present invention can be used solely or after being formulated into pharmaceutical compositions for the prophylaxis and treatment of infectious diseases.

The agent for the prophylaxis and treatment of infectious diseases comprising Compound (I) or its pharmaceutically acceptable salt of the present invention exhibits the above-mentioned excellent actions by oral administration, and is normally administered orally as an oral agent. Since Compound (I) and its pharmeceutically acceptable salt are noticeably sweet, oral agents which are easily taken can be prepared.

The agent for the prophylaxis and treatment of infectious diseases of the present invention can be prepared by means known per se by admixing with pharmaceutical excipients. Said excipients include starch, lactose, sugar, calcium carbonate and calcium phosphate.

The agent for the prophylaxis and treatment of bacterial infectious diseases to be administered orally preferably also contains an organic acid, by which solubility of Compound (I) and its pharmaceutically acceptable salt in digestive tract can be enhanced, rendering absorption into blood easier. The organic acid is subject to no particular limitation so long as it is pharmaceutically acceptable, and preferably includes, for example, organic carboxylic acids such as maleic acid, fumaric acid, tartaric acid, citric acid, succinic acid, malic acid, oxalic acid, mandelic acid, malonic acid and benzoic acid. Said organic acid is present in amounts varying from 0.01 to 20 moles, preferably from 0.02 to 2 moles based on one mole of Compound (I) or its salt.

The agent for the prophylaxis and treatment of bacterial infectious diseases to be administered orally preferably further contains other additives such as binders (e.g. starch, gum arabic, carboxymethylcellulose, hydroxypropylcellulose, crystalline cellulose), lubricants (e.g. magnesium stearate, talc), and disintegrators (e.g. carboxymethylcellulose calcium, talc). Each components are mixed, and formulated into preparation forms suitable for oral administration, such as capsules, tablets, fine granules, granules and dry syrups by means known per se.

The agent for the prophylaxis and treatment of bacterial infectious diseases containing Compound (I) or its pharmaceutically acceptable salt of the present invention is swiftly absorbed from the digestive tract when administered orally, and immediately after absorption, hydrolyzed by enzymes in the body into Compound (A) or its pharmaceutically acceptable salt, enabling exertion of its superior antimicrobial activities.

While the dose of Compound (I) and its pharmaceutically acceptable salt varies depending on administration target, symptom, and so on, it is about 1 to 40 mg/kg body weight on the basis of Compound (A) for single dose which is orally administered 1 to 4 times per day in case of an adult with suppurative diseases.

Compound (I) and its pharmaceutically acceptable salt of the present invention may be co-administered with, for example, agents having antimicrobial activities such as antimicrobial agent (e.g. penicillins, aminoglucosides, cephalosporins), and agents for the treatment of systemic symptoms caused by bacterial infections (e.g. antipyretic, analgesic, antiphlogistic).

Experimental Example 1 (Oral administration)
(1) Test method

The compound of the present invention (20 mg/kg) to be mentioned in the following Examples was orally administered to rabbits (3 per group), and recovery from urine and concentration in serum of Compound (A) converted by hydrolysis were determined by the bioassay method using *Escherichia coli*.

(2) Test results

| Compound | Recovery from urine (0–8 hrs) | Concentration in blood (μg/ml) | | | | | | |
|---|---|---|---|---|---|---|---|---|
| | | 0.125 hr | 0.25 hr | 0.5 hr | 1.0 hr | 2.0 hr | 4.0 hr | 6.0 hr |
| Compound of Ex. 3 | 40.9% | 0.6 | 2.5 | 6.0 | 5.5 | 2.3 | 0.5 | 0.1 |

Experimental Example 2 (Sweetness)

(1) Test method 0.01, 0.02, 0.03, 0.04 and 0.05% aqueous solutions of the compounds of Example 3 and Example 6 were respectively prepared, and compared with 1, 2, 3, 4, 5, 6, 7, 8, 9 and 10% aqueous solutions of sucrose for the sweetness.

(2) Test results

| Compound | Sweetness (sucrose = 1) |
|---|---|
| Compund of Example 3 | ca. 300 |
| Compound of Example 6 | ca. 10 |

EXAMPLE 1

2-[2-(Boc-L-alanyl)aminothiazol-4-yl]-2-methoxyiminoacetic acid (syn-isomer)

(1) Ethyl 2-(2-aminothiazol-4-yl)glyoxylate (4.0 g) and Boc-L-alanine (5.67 g) were dissolved in 40 ml of N,N-dimethylformamide (hereafter abbreviated as DMF), and thereto was added 1-ethyl-3-(3'-dimethylaminopropyl)carbodiimide hydrochloride (5.74 g) under ice-cooling followed by addition of 4-dimethylaminopyridine (0.4 g). The mixture was stirred at room temperature for 5 hours. Water (400 ml) was added thereto, and the mixture was extracted twice with ethyl acetate (300 ml). The ethyl acetate layer was washed with 10% aqueous solution of citric acid (200 ml), saturated aqueous solution of sodium bicarbonate (200 ml) and saturated brine (200 ml) in this order, and dried over anhydrous sodium sulfate. The ethyl acetate was distilled off under reduced pressure, and the residue was subjected to silica gel column chromatography eluted with benzene-ethyl acetate. The object fraction was concentrated to give 5.30 g of ethyl 2-[2-(Boc-L-alanyl)aminothiazol-4-yl]glyoxylate.

(2) The product obtained in (1) above (5.30 g) was dissolved in ethanol (28 ml), and thereto was added 2N aqueous solution of sodium hydroxide (7.13 ml), and the mixture was stirred at room temperature for 2 hours. Water (150 ml) was added thereto, and the mixture was extracted twice with ethyl acetate (50 ml). The ethyl acetate layer was extracted with saturated aqueous solution of sodium bicarbonate (50 ml). The combined water layer was acidified with citric acid and extracted four times with ethyl acetate (200 ml). The ethyl acetate layer was washed with saturated brine (100 ml) and dried over anhydrous sodium sulfate. The ethyl acetate was distilled off under reduced pressure to give 4.88 g of 2-[2-(Boc-L-alanyl)aminothiazol-4-yl]glyoxylic acid.
IR (Nujol, cm$^{-1}$): 1690, 1550
NMR (DMSO$_{d-6}$, δppm): 1.26 (d, J=7.0 Hz, 3H, —CH$_3$), 1.42 (s, 9H, —OC(CH$_3$)$_3$), 3.80~4.60 (m, 1H, —CH<) 5.00~9.80 (br, 1H, —CO$_2$H), 7.22 (d, J=9.0 Hz, 1H, —NH—), 8.34 (s, 1H, thiazole C$_5$—H), 12.60 (br, 1H, thiazole C$_2$—NH—)

(3) The product obtained in (2) above (4.88 g) was dissolved in a mixture of tetrahydrofuran (hereafter abbreviated as THF) and water (2:1, 300 ml), and thereto was added methoxyamine (0.74 g), and the mixture was stirred at pH 5 for 2 hours. The THF was distilled off under reduced pressure, and the residue was acidified with citric acid and extracted three times with ethyl acetate (200 ml). The ethyl acetate layer was washed with saturated brine (100 ml) and dried over anhydrous sodium sulfate. The solution was concentrated under reduced pressure to 70 ml. Dicyclohexylamine (2.84 ml) was added thereto, and the mixture was stirred under ice-cooling for half an hour for crystalization. The precipitated crystals were separated by filtration, suspended in ethyl acetate (400 ml), washed with 10% aqueous solution of citric acid (200 ml) and saturated brine (200 ml) and then dried over anhydrous sodium sulfate. The ethyl acetate was distilled off under reduced pressure to give 3.71 g of the title compound.

IR (Nujol, cm$^{-1}$): 1700, 1550

NMR (DMSO$_{d-6}$, δppm): 1.26 (d, J=7.0 Hz, 3H, —CH$_3$), 1.42 (s, 9H, —OC(CH$_3$)$_3$), 3.85 (s, 3H, —OCH$_3$), 3.90~4.50 (m, 1H, —CH<), 6.70~7.36 (br, 1H, —NH—), 7.54 (s, 1H, thiazole C$_5$—H), 5.00~9.00 (br, 1H, —CO$_2$H), 12.44 (br.s, 1H, thiazole C$_2$—NH—)

EXAMPLE 2

2-[2-(Boc-L-alanyl)aminothiazol-4-yl]-2-methoxyiminoacetic acid (syn-isomer)

(1) Ethyl 2-(2-aminothiazol-4-yl)methoxyiminoacetate (syn-isomer) (5.0 g) and Boc-L-alanine (6.19 g) were dissolved in DMF(50 ml), and thereto was added 1-ethyl-3-(3'-dimethylaminopropyl)-carbodiimide hydrochloride (6.27 g) under ice-cooling followed by addition of 4-dimethylaminopyridine (430 mg). The mixture was stirred at room temperature for 5 hours. Water (500 ml) was added thereto, and the mixture was extracted twice with ethyl acetate (300 ml). The ethyl acetate layer was washed with 10% aqueous solution of citric acid (200 ml), saturated aqueous solution of sodium bicarbonate (200 ml) and saturated brine (200 ml) in this order, and dried over anhydrous sodium sulfate. The ethyl acetate was distilled off under reduced pressure, and the residue was subjected to silica gel column chromatography eluted with benzene-ethyl acetate. The object fraction was concentrated to give 5.90 g of ethyl 2-[2-(Boc-L-alanyl)aminothiazol-4-yl]-2-methoxyiminoacetate (syn-isomer).

IR (Nujol, cm$^{-1}$); 1740, 1690

NMR (DMSO$_{d-6}$, δppm); 1.17 (t, J=6 Hz, 3H, —CH$_3$), 1.25 ( d, J=7 Hz, 3H, —CH$_3$ ), 1.44 ( s, 9H, —OC(CH$_3$)$_3$), 3.88 ( s, 3H, —OCH$_3$), 3.90~4.50 (m, 1H, —CH<), 4.00 (q, J=6 Hz, 2H, —CH$_2$—), 6.60~7.40 (br, 1H, —NH—), 7.55 (s, 1H, thiazole C$_5$—H), 12.45 (br.s, 1H, thiazole C$_2$—NH—)

(2) The product obtained in (1) above (5.90 g) was dissolved in ethanol (29 ml), and thereto was added 2N aqueous solution of sodium hydroxide (7.35 ml), and the mixture was stirred at room temperature for 2 hours. Water (150 ml) was added thereto, and the mixture was washed twice with ethyl acetate (50 ml). The ethyl acetate layer was extracted with saturated aqueous solution of sodium bicarbonate (50 ml). The combined water layer was acidified with citric acid and extracted four times with ethyl acetate (200 ml). The ethyl acetate layer was washed with saturated brine (100 ml) and dried over anhydrous sodium sulfate. The ethyl acetate was distilled off under reduced pressure to give 4.97 g of the title compound.

The properties of the thus-obtained compound were identical with those of the title compound of Example 1.

EXAMPLE 3

Pivaloyloxymethyl 7-[2-(2-L-alanylaminothiazol-4-yl)-2-methoxyiminoacetamide]-3-cephem-4-carboxylate hydrochloride (syn-isomer)

(1) A mixture of dry ethyl acetate (1.82 ml) and dry DMF (0.36 ml) was cooled to —10° C. Phosphorus oxychloride (0.37 ml) was added thereto, and the mixture was stirred at said temperature for 20 minutes. A solution of the compound of Example 1 (1.35 g) in dry methylene chloride (8.0 ml) was added thereto, and the mixture was stirred at a temperature between —10° to —5° C. for 30 minutes. On the other hand, pivaloyloxymethyl 7-amino-3-cephem-4-carboxylate (0.95 g) was dissolved in dry methylene chloride (12 ml), and N-trimethylsilylacetamide (0.79 g) was added thereto, and the mixture was cooled to —15° C. Thereto was dropwise added the aforementioned solution, and the mixture was stirred at said temperature for 45 minutes. Ethyl acetate (200 ml) was added thereto, and the mixture was washed with 5% aqueous solution of sodium bicarbonate (100 ml) and saturated brine (100 ml). After drying over anhydrous sodium sulfate, the solvent was distilled off under reduced pressure. The residue was subjected to silica gel column chromatography eluted with benzene-ethyl acetate. The object fraction was concentrated to give 1.32 g of pivaloyloxymethyl 7-[2-(Boc-L-alanyl)aminothiazol-4-yl]-2-methoxyimino-3-cephem-4-carboxylate (synisomer).

IR (Nujol,cm$^{-1}$): 1790, 1750, 1685

NMR (DMSO$_{d-6}$, δppm): 1.13 (d, J=7.0 Hz, 3H, —CH$_3$), 1.16 (s, 9H, —COC(CH$_3$)$_3$), 1.36 (s, 9H, —OC(CH$_3$)$_3$), 3.50~3.80 (m, 2H, C$_2$—H$_2$), 3.90~4.40 (m, 1H, —CH<), 5.14 ( d, J=5.0 Hz, 1H, C$_6$—H), 5.70~6.10 ( m, 3H, C$_7$—H, —CO$_2$CH$_2$—), 6.50~6.80 (br, 1H, C$_3$—H), 6.90~7.20 (br, 1H, —NH—), 7.32 (s, 1H, thiazole C$_5$—H), 9.17 (d, J=9.0 Hz, 1H, —CONH—), 12.40 (br.s, 1H, thiazole C$_2$—NH—)

(2) The product obtained in (1) above (1.30 g) was dissolved in methylene chloride (3.20 ml), and thereto was added anisole (1.30 ml) and trifluoroacetic acid (6.50 ml) at room temperature, and the mixture was stirred for 30 minutes at said temperature. The mixture was then poured into isopropyl ether (150 ml), and the precipitate was separated by filtration. A cooled ethyl acetate (100 ml) was added thereto, and the mixture was washed with cooled 1% aqueous solution of sodium bicarbonate (50 ml) and then with cooled saturated brine and dried over anhydrous sodium sulfate. The ethyl acetate was distilled off under reduced pressure. The residue was dissloved in methylene chloride (2.0 ml), and 0.3 ml of 6.1N hydrogen chloride in isopropanol was added thereto. The mixture was poured into isopropyl ether (50 ml), and the precipitate was separated by filtration to give 530 mg of the title compound.

IR (Nujol,cm$^{-1}$): 1775, 1750, 1700, 1670

NMR (DMSO$_{d-6}$, δppm): 1.20 (s, 9H, —COC(CH$_3$)$_3$), 1.52 (d, J=7.0 Hz, 3H, —CH$_3$), 3.70 (br.s, 2H, C$_2$—H$_2$), 3.90 (s, 3H, —OCH$_3$), 3.90~4.30 (br, 1H, —CH<), 5.16 (d, J=5 Hz, 1H, C$_6$—H), 5.65~6.10 (m, 3H, C$_7$—H, —CO$_2$CH$_2$—), 6.65 (br, 1H, C$_3$—H), 7.44 (s, 1H, thiazole C$_5$—H), 8.4~8.9 (br, 3H, —N+H$_3$), 9.68 (d, J=8.4 Hz, 1H, —CONH—), 13.00 (br, 1H, thiazole C$_2$—NH—)

EXAMPLE 4

Pivaloyloxymethyl
7-[2-(2-L-alanylaminothiazol-4-yl)-2-methox-yiminoacetamide]-3-cephem-4-carboxylate hydrochloride (syn-isomer)

(1) 2-(2-aminothiazol-4-yl)-2-methoxyiminoacetic acid (syn-isomer) (2.85 g) and pivaloyloxymethyl 7-amino-3-cephem-4-carboxylate (4.0 g) were dissolved in methylene chloride (40 ml), and pyridine (3.40 ml) and phosphorus oxychloride (2.62 ml) were added thereto at −5° C., and the mixture was stirred at said temperature for 30 minutes. Thereto was added ethyl acetate (100 ml), and the mixture was washed with 10% aqueous solution of citric acid (50 ml) and saturated brine (50ml) in this order, and dried over anhydrous sodium sulfate. The solvent was distilled off under reduced pressure, and the residue was subjected to silica gel column chromatography eluted with benzene-ethyl acetate. The object fraction was concentrated to give 4.60 g of pivaloyloxymethyl 7-[2-(2-aminothiazol-4-yl)-2-methoxyiminoacetamide]-3-cephem-4-carboxylate (syn-isomer).

IR (Nujol,cm$^{-1}$): 1750, 1630,

NMR (DMSO$_{d-6}$, δppm): 1.15 (s, 9H, -COC(CH$_3$)$_3$), 3.50~3.80 ( br, 2H, C$_2$—H$_2$), 3.85 ( s, 3H, —OCH$_3$), 5.15 (d, J=5.0 Hz, 1H, C$_6$—H), 5.87 (d×d, J=5.0 Hz, 9.0 Hz, 1H, C$_7$—H), 5.70~6.10 (m, 2H, —CO$_2$C-H$_2$—), 6.50~6.80 (m, 1H, C$_3$—H), 6.80 (s, 1H, thiazole C$_5$—H), 6.90~7.30 (br, 2H, —NH$_2$), 9.60 (d, J=9.0 Hz, 1H, —CONH—)

(2) The product obtained in (1) above (4.51 g) and Boc-L-alanine (2.15 g) were dissolved in methylene chloride (50 ml), and thereto was added 1-ethyl-3-(3'-dimethylaminopropyl)carbodiimide hydrochloride (2.38 g) under ice-cooling followed by addition of 4-dimethylaminopyridine (220 mg). The mixture was stirred at room temperature for 2 hours. Methylene chloride (80 ml) was added thereto, and the mixture was washed with 10% aqueous solution of citric acid (100 ml), saturated aqueous solution of sodium bicarbonate (100 ml) and saturated brine (100 ml) in this order and dried over anhydrous sodium sulfate. The methylene chloride was distilled off under reduced pressure, and the residue was subjected to silica gel column chromatography eluted with benzene-ethyl acetate. The object fraction was concentrated to give 2.25 g of pivaloyloxymethyl 7-[2-(Boc-L-alanylaminothiazol-4-yl)-2-methoxyiminoacetamide]-3-cephem-4-carboxylate (syn-isomer).

The properties of the thus-obtained compound were identical with those of the compound obtained in Example 3 (1).

(3) The product obtained in (2) above (2.20 g) was subjected to a reaction in the same manner as in Example 3 (2) to give 0.9 g of the title compound.

The properties of the thus-obtained compound were identical with those of the title compound of Example 3.

EXAMPLE 5

Pivaloyloxymethyl
7-[2-(2-L-alanylaminothiazol-4-yl)-2-methox-yiminoacetamide]-3-cephem-4-carboxylate hydrochloride (syn-isomer)

(1) A mixture of dry ethyl acetate (0.9 ml) and dry DMF (0.18 ml) was cooled to −10° C. Phosphorus oxychloride (0.19 ml) was added thereto, and the mixture was stirred at said temperature for 20 minutes. A solution of the title compound of Example 1 (1.35 g) in dry methylene chloride (4.0 ml) was added thereto, and the mixture was stirred at a temperature between −10° to −5° C. for 30 minutes. On the other hand, 7-amino-3-cephem-4-carboxylic acid (0.31 g) was suspended in dry methylene chloride (6.0 ml), and N-trimethylsilylacetamide (1.42 g) was added thereto, and the mixture was stirred at 30° C. for 30 minutes for homogeneous dissolution and then cooled to −5° C. Thereto was dropwise added the aforementioned solution, and the mixture was stirred at −10° C. for 1 hour. Ethyl acetate (150 ml) was added thereto, and the mixture was washed with 10% aqueous solution of citric acid (50 ml), and the aqueous layer was further extracted with ethyl acetate (50 ml). The combined ethyl acetate layer was washed twice with saturated brine (70 ml). After drying over anhydrous sodium sulfate, the solution was concentrated under reduced pressure and poured into isopropyl ether (300 ml). The precipitate was separated by filtration to give 0.81 g of 7-[2-(Boc-L-alanylaminothiazol-4-yl)-2-methoxyiminoacetamide]-3-cephem-4-carboxylic acid (syn-isomer) as a powder.

IR (Nujol,cm$^{-1}$) :1770, 1670

NMR (DMSO$_{d-6}$, δppm): 1.08 (d, J=7.0 Hz, 3H, —CH$_3$ ), 1.45 (s, 9H, —OC(CH$_3$)$_3$), 3.51~3.79 (m, 2H, C$_2$—H$_2$), 3.89 ( s, 3H, —OCH$_3$), 3.92~4.40 (m, 1H, —CH<), 4.57~7.05 (br, 1H, —CO$_2$H), 5.14 (d, J=5.0 Hz, 1H, C$_6$—H), 5.82 ( d×d, J=5.0 Hz, 9.0 Hz, 1H, C$_7$—H), 6.50~6.80 (m, 1H, C$_3$—H), 6.90~7.21 (br, 1H, —NH—), 7.35 (s, 1H, thiazole C$_5$—H), 9.20 (d, J=9.0 Hz, 1H, —CONH—), 12.40 (br.s, 1H, thiazole C$_2$—NH—)

(2) The product obtained in (1) above (0.81 g) was dissolved in DMF (10 ml), and thereto was added potassium acetate (130 mg), and the mixture was cooled to −20° C. Iodomethyl pivalate (481 mg) was added thereto, and the mixture was stirred at said temperature for 1 hour. Ethyl acetate (200 ml) was added thereto, and the mixture was washed with water (100 ml) and saturated brine (100 ml) and dried over anhydrous sodium sulfate. The solvent was distilled off under reduced pressure, and the residue was subjected to silica gel column chromatography eluted with benzene-ethyl acetate. The object fraction was concentrated to give 0.56 g of pivaloyloxymethyl 7-[2-(Boc-L-alanyl)amino-thiazol-4-yl)-2-methoxyiminoacetamide]- 3-cephem-4-carboxylate (syn-isomer).

The properties of the thus-obtained compound were identical with those of the compound obtained in Example 3 (1).

(3) The product obtained in (2) above (0.56 g) was subjected to a reaction in the same manner as in Example 3 (2) to give 0.22 g of the title compound. The properties of the thus-obtained compound were identical with those of the title compound of Example 3.

In the same manner as in Examples 3 to 5, the following compound was synthesized.

EXAMPLE 6

1-Ethoxycarbonyloxyethyl 7-[2-(2-L-alanylaminothiazol-4-yl)-2methoxyiminoacetamide]-3-cephem-4-carboxylate hydrochloride (syn-isomer)

IR (Nujol,cm$^{-1}$): 1775, 1700, 1675

NMR (DMSO$_{d\text{-}6}$, δppm): 1.21 ( t, J=7.0 Hz, 3H, —CH$_3$), 1.50 ( d, J=6.0 Hz, 6H, —CH$_3$×2), 3.50~3.78 ( m, 2H, C$_2$—H$_2$), 3.88 (s, 3H, —OCH$_3$), 3.90~4.35 (m, 1H, —CH<), 4.13 (q, J=7.0 Hz, 2H, —CH$_2$—), 5.13 (d, J=5.0 Hz, 1H, C$_6$—H), 5.91 (d×d, J=5.0, 9.0 Hz, 1H, C$_7$—H), 6.47~6.97 (m, 2H, —CO$_2$CH<, C$_3$—H), 7.42 (s, 1H, thiazole C$_5$—H), 8.00~8.90 (br, 3H, —N$^+$H$_3$), 9.63 (d, J=9.0 Hz, 1H, —CONH—), 12.98 (br.s, 1H, thiazole C$_2$—NH—)

In the same manner as in Examples 1 to 5, the following compound was synthesized.

EXAMPLE 7

Pivaloyloxymethyl 7-[2-(2-D-alanylaminothiazol-4-yl)-2-methoxyiminoacetamide]-3-cephem-4-carboxylate hydrochloride (syn-isomer )

IR (Nujol,cm$^{-1}$) :3500, 1790, 1780, 1755, 1710, 1690, 1665

NMR (DMSO$_{d\text{-}6}$, δppm): 1.20 (s, 9H, —COC(CH$_3$)$_3$), 1.53 ( d, J=7.0 Hz, 3H, —CH$_3$), 3.66 (br. s, 2H, C$_2$—H$_2$), 3.90~4.50 ( m, 1H, —CH<), 3.90 (s, 3H, —OCH$_3$), 5.16 (d, J=5.0 Hz, 1H, C$_6$—H), 5.67~6.20 ( m, 3H, C$_7$—H, —CO$_2$CH$_2$—), 6.44~6.90 (m, 1H, C$_3$—H), 7.45 ( s, 1H, thiazole C$_5$—H), 8.20~9.20 ( br, 3H, —N+H$_3$), 9.75 ( d, J=9.0 Hz, 1H, —CONH—), 12.76~13.40 (br, 1H, thiazole C$_2$—NH—)

The following compounds are prepared according to any of the methods described in Examples 3 to 5. (1) 1-Acetoxyethyl 7-[2-(2-L-alanylaminothiazol-4-yl)-2-methoxyiminoacetamide]-3-cephem-4-carboxylate hydrochloride (syn-isomer) (2) 1-Ethoxycarbonyloxyethyl 7-[2-(2-L-alanylaminothiazol-4-yl)-2-ethoxyiminoacetamide]-3-cephem-4-carboxylate hydrochloride (syn-isomer) (3) Pivaloyloxymethyl 7-[2-(2-L-alanylaminothiazol-4-yl)-2-ethoxyiminoacetamide]-3-cephem-4-carboxylate hydrochloride (syn-isomer) (4) 1-Acetoxyethyl 7-[2-(2-L-alanylaminothiazol-4-yl)-2-ethoxyiminoacetamide]-3-cephem-4-carboxylate hydrochloride (syn-isomer) (5) 1-Ethoxycarbonyloxyethyl 7-[2-(2-L-alanylaminothiazol-4-yl)-2-hydroxyiminoacetamide]-3-cephem-4-carboxylate hydrochloride (syn-isomer) (6) 1-iso-Propoxycarbonyloxyethyl 7-[2-(2-L-alanylaminothiazol-4-yl)-2-hydroxyiminoacetamide]-3-cephem-4-carboxylate hydrochloride (syn-isomer) (7) 1-iso-Propoxycarbonyloxyethyl 7-[2-(2-L-alanylaminothiazol-4-yl)-2-ethoxyiminoacetamide]-3-cephem-4-carboxylate hydrochloride (syn-isomer) (8) 1-Pivaloyloxyethyl 7-[2-(2-L-alanylaminothiazol-4-yl)-2-methoxyiminoacetamide]-3-cephem-4-carboxylate hydrochloride (syn-isomer) (9) 1-Pivaloyloxyethyl 7-[2-(2-L-alanylaminothiazol-4-yl)-2-ethoxyiminoacetamide]-3-cephem-4-carboxylate hydrochloride (syn-isomer)

EXAMPLE 8

1-Cyclohexyloxycarbonyloxyethyl 7-[2-(2-L-alanylaminothiazol-4-yl)-2-methoxyiminoacetamide]-3-cephem-4-carboxylate hydrochloride (syn-isomer)

IR (Nujol,cm$^{-}$):3250, 1790, 1760, 1690, 1660

NMR (DMSO$_{d\text{-}6}$, δppm): 0.96~2.20 (m, 10H,

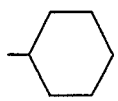

1.52 ( d, J=7.0 Hz, 6H, —CH$_3$×2), 3.66 (br. s, 2H, C$_2$—H$_2$), 3.93 (s, 3H, —OCH$_3$), 4.00~4.32 (m, 1H, —CH<), 4.32~4.86 (m, 1H,

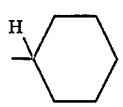

5.16 (d, J=5.0 Hz, 1H, C$_6$—H), 5.94 (d×d, J=5.0, 9.0 Hz, 1H, C$_7$—H), 6.46~7.02 (m, 2H, —CH<, C$_3$—H), 7.46 (s, 1H, thiazole C$_5$—H), 7.96~9.02 (br. 3H, —N$^+$H$_3$), 9.73 (d, J=9.0 Hz, 1H, —CONH—), 12.80~13.24 (br, 1H, thiazole C$_2$—NH—)

EXAMPLE 9

1-iso-Propoxycarbonyloxyethyl 7-[2-(2-L-alanylaminothiazol-4-yl)-2-methoxyiminoacetamide]-3-cephem-4-carboxylate hydrochloride (syn-isomer)

IR (Nujol,cm$^{-1}$) :3150, 1780, 1765, 1705, 1670

NMR (DMSO$_{d\text{-}6}$, δppm): 1.28 (d, J=7.0 Hz, 6H, —(CH$_3$)$_2$), 1.54 (d, J=7.0 Hz, 6H, —CH$_3$×2), 3.50~3.84 (m, 2H, C$_2$—H$_2$), 3.95 (s, 3H, —OCH$_3$), 4.00~4.40 (m, 1H, —CH<), 4.46~5.10 (m, 1H, —CH<), 5.17 (d, J=5.0 Hz, 1H, C$_6$—H), 5.97 (d×d, J5.0, 9.0 Hz, 1H, C$_7$—H), 5.49~7.10 (m, 2H, —CH, C$_3$—H), 7.51 (s, 1H, thiazole C$_5$—H), 7.90~10.20 (br. 3H, —N$^+$H$_3$), 9.75 (d, J=9.0 Hz, 1H, —CONH—), 11.80~14.00 (br, 1H, thiazole C$_2$—NH—)

EXAMPLE b 10

2, 2-Dimethylbutyryloxymethyl 7-[2-(2-L-alanylaminothiazol-4-yl)-2-methoxyiminoacetamide]-3-cephem-4-carboxylate hydrochloride (syn-isomer)

IR (Nujol,cm$^{-1}$):3350, 1790, 1755, 1715, 1680

NMR (DMSO$_{d\text{-}6}$, δppm ): 1.00 (s, 9H—(CH$_3$)$_3$), 1.52 ( d, J=7.0 Hz, 3H, —CH$_3$), 2.28 (s, 2H, —CH$_2$—), 3.72 (br.s, 2H, C$_2$—H$_2$), 3.94 (s, 3H, —OCH$_3$), 3.90~4.40 (m, 1H, —CH<), 5.18 (d, J=5.0 Hz, 1H, C$_6$—H), 5.60~6.18 (m, 3H, —CO$_2$CH$_2$—, C$_7$—H), 6.44~6.85 (m, 1H, C$_3$—H), 7.48 (s, 1H, thiazole C$_5$—H), 7.98~10.00 (br, 3H, —N$^+$H$_3$), 9.72 (d, J=9.0 Hz, 1H, —CONH—), 11.00~14.00 (br, 1H, thiazole C$_2$—NH—)

EXAMPLE 11 iso-Butyryloxymethyl 7-[2-(2-L-alanylaminothiazol-4-yl)-2-methoxyiminoacetamide]-3-cephem-4-carboxYlate hydrochloride (syn-isomer)

IR (Nujol,cm$^{-1}$) :3140, 1780, 1750, 1705, 1670
NMR (DMSO$_{d-6}$, δppm): 1.15 (d, J=7.0 Hz, 6H, —(CH$_3$)$_2$), 1.55 (d, J=7.0 Hz, 3H, —CH$_3$), 2.30~3.00 (s, 1H, —CH<), 3.60~3.85 ( m, 2H, C$_2$—H$_2$), 3.95 ( s, 3H, —OCH$_3$), 3.85~4.50 (m, 1H, —CH<), 5.20 (d, J=5.0 Hz, 1H, C$_6$—H), 5.60~6.15 ( m, 3H, C$_7$—H, —CO$_2$CH$_2$—), 6.40~6.90 (m, 1H, C$_3$—H), 7.53 (s, 1H, thiazole C$_5$—H), 8.00~9.40 (br, 3H, —N$^+$H$_3$), 9.75 (d, J=9.0 Hz, 1H, —CONH—), 13.10 (br, 1H, thiazole C$_2$—NH—)

EXAMPLE 12 iso-Butyryloxymethyl 7-[2-(2-L-alanylaminothiazol-4-yl )-2-methoxyiminoacetamide]-3-cephem-4-carboxylate hydrochloride (syn-isomer)

IR (Nujol,cm$^{-1}$): 3400, 3150, 1780, 1750, 1705, 1670
NMR (DMSO$_{d-6}$, δppm): 1.10 (d, J=7.0 Hz, 6H, —(CH$_3$, CH$_3$)$_2$), 1.50 (d, J=7.0 Hz, 6H, —CH$_3$), 2.20~2.90 (m, 1H, —CH<), 3.30~3,80 (m, 2H, C$_2$—H$_2$), 3.90 (s, 3H, —OCH$_3$), 3.80~4.40 (m, 1H, —CH<), 5.25 (d, J=5.0 Hz, 1H C$_6$—H), 5.95 (d×d, J=5.0 Hz, 9.0 Hz, 1H, C$_7$—H), 6.50~7.20 (m, 2H, C$_3$—H, —CH<), 7.48 (s, 1H, thiazole C$_5$—H), 8.20~9.00 (br. 3H, —N$^+$H$_3$), 9.70 ( d, J=9.0 Hz, 1H, —CONH—), 13.10 (br, 1H, thiazole C$_2$—NH—)

EXAMPLE 13 iso-Valeryloxymethyl 7-[2-(2-L-alanylaminothiazol-4-yl )-2-methoxyiminoacetamide]-3-cephem-4-carboxylate hydrochloride (syn-isomer )

IR (Nujol,cm$^{-1}$): 1785, 1750, 1715, 1680
NMR (DMSO$_{d-6}$, δppm): 0.90 (d, J=6.0 Hz, 6H, —(CH$_3$)$_2$), 1.45 (d, J=6.0 Hz, 3H, —CH$_3$), 1.70~2.40 (m, 3H, —CH$_2$CH<), 3.65 (br.s, 2H, C$_2$—H$_2$), 3.80~4.30 (m, 1H, —CH<), 3.90 (s, 3H, —OCH$_3$), 5.15 (d, J=5.0 Hz, 1H, C$_6$—H), 5.6~6.1 ( m, 1 H, C$_7$—H), 5.85 ( s, 2H, —CO$_2$CH$_2$—), 6.40~6.80 (m, 1H, C$_3$—H), 7.45 (s, 1H, thiazole C$_5$—H), 7. 60~11.00 (br, 4H, —N$^+$H$_3$, thiazole C$_2$—NH—), 9.70 (d, J=8.0 Hz, 1H, —CONH—)

FORMULATION EXAMPLE 1

Tablets of the following. composition are prepared by a conventional method.

| | |
|---|---|
| Compound of Example 3 | 125 mg potency |
| Polyvinylpyrrolidone | 20 mg |
| Starch | 20 mg |
| Magnesium stearate | 2.0 mg |

FORMULATION EXAMPLE 2

Tablets of the following composition are prepared by a conventional method.

| | |
|---|---|
| Compound of Example 3 | 250 mg potency |
| Citric acid | 50 mg |
| Starch | 20 mg |
| Magnesium stearate | 3.0 mg |

FORMULATION EXAMPLE 3

Tablets of the following composition are prepared by a conventional method.

| | |
|---|---|
| Compound of Example 3 | 500 mg potency |
| Starch | 20 mg |
| Hydroxypropylcellulose | 3 mg |
| Magnesium stearate | 5 mg |

FORMULATION EXAMPLE 4

Capsules are prepared by mixing the compound of Example 3 with tartaric acid, followed by a conventional capsule filling.

| | |
|---|---|
| Compound of Example 3 | 125 mg potency |
| Tartaric acid | 25 mg |
| Magnesium stearate | 1 mg |
| Starch | sufficient amount |
| Total amount | 300 mg |

FORMULATION EXAMPLE 5

Capsules of the followng composition are prepared according to Formulation Example 4.

| | |
|---|---|
| Compound of Example 3 | 125 mg potency |
| Magnesium stearate | 2 mg |
| Lactose | suffiecient amount |
| Total amount | 200 mg |

FORMULATION EXAMPLE 6

Fine granules of the followng composition are prepared by a conventional method.

| | |
|---|---|
| Compound of Example 3 | 62.5 mg potency |
| Lactose | 22 mg |
| Purified water | 0.03 ml |
| Starch | 10 mg |
| Hydroxypropylcellulose | 3 mg |

FORMULATION EXAMPLE 7

Granules of the following composition are prepared by a conventional method.

| | |
|---|---|
| Compound of Example 3 | 62.5 mg potency |
| Lactose | 25 mg |
| Starch | 5 mg |
| Purified water | 0.03 ml |
| Hydroxypropylcellulose | 5 mg |

The present invention has been properly and sufficiently explained in the foregoing specification including Examples, which can be changed or modified within the spirit and scope of the present invention.

What is claimed is:

1. A cephalosporin compound of the formula (I)

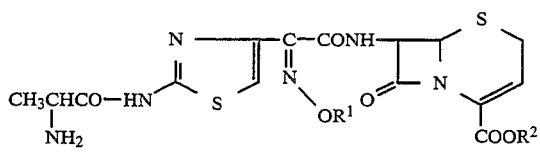

wherein $R^1$ is hydrogen atom or lower alkyl, and $R^2$ is 1-alkanoyloxyalkyl or 1-alkoxycarbonyloxyalkyl except 1-cyclohexyloxycarbonyloxyethyl, or its pharmaceutically acceptable salt.

2. A cephalosporin compound according to claim 1, wherein $R^2$ is selected from the group consisting of acetoxymethyl, propionyloxymethyl, n-butyryloxymethyl, isovaleryloxymethyl, pivaloyloxymethyl, 1-acetoxyethyl, 1-propionyloxyethyl, 1-isobutyryloxyethyl, 1-n-valeryloxyethyl, 1-isovaleryloxyethyl, 1-pivaloyloxyethyl, 1-ethoxycarbonyloxethyl, and 1-isopropoxycarbonyloxyethyl, or its pharmaceutically acceptable salt.

3. A cephalosporin compound according to claim 1 which is selected from the following compounds, or its pharmaceutically acceptable salt;
   (1) pivaloyloxymethyl 7-[2-(2-L-alanylaminothiazol-4-yl )-2-methoxyiminoacetamide]-3-cephem-4-carboxylate hydrochloride (syn-isomer)
   (2) 1-ethoxycarbonyloxyethyl 7-[2-(2-L-alanylaminothiazol-4-yl )-2-methoxyiminoacetamide]-3-cephem-4-carboxylate hydrochloride (syn-isomer).

4. A cephalosporin compound according to claim 1 or its pharmaceutically acceptable salt which is a syn-isomer.

5. A cephalosporin compound according to claim 1, which is an L compound at the carbon atom marked with * in formula (I) of Claim 1, or its pharmaceutically acceptable salt.

6. An agent to be administered orally for the prophylaxis and treatment of bacterial infectious diseases, which comprises an effective amount of a cephalosporin compound of the formula (I)

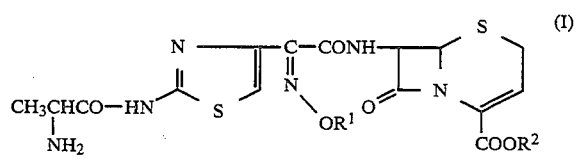

wherein $R^1$ is hydrogen atom or lower alkyl, and $R^2$ is 1-alkanoyloxyalkyl or 1-alkoxycarbonyloxyalkyl except 1-cyclohexyloxycarbonyloxyethyl, or its pharmaceutically acceptable salt as an active ingredient and a pharmaceutically acceptable excipient.

7. An agent to be administered orally for the prophylaxis and treatment of bacterial infectious diseases according to claim 6, which contains a pharmaceutically acceptable organic acid.

8. An agent to be administered orally for the prophylaxis and treatment of bacterial infectious diseases according to claim 7, wherein the organic acid is an organic carboxylic acid.

9. An agent to be administered orally for the prophylaxis and treatment of bacterial infectious diseases according to claim 8, wherein the organic carboxylic acid is at least one member selected from the group consisting of maleic acid, fumaric acid, tartaric acid, citric acid, succinic acid, malic acid, oxalic acid, mandelic acid, malonic acid and benzoic acid.

10. An agent to be administered orally for the prophylaxis and treatment of bacterial infectious diseases according to claim 7, wherein the organic acid comprises from 0.01 to 20 moles based on one mole of the compound of formula (I) or its acid addition salt.

* * * * *

UNITED STATES PATENT AND TRADEMARK OFFICE
CERTIFICATE OF CORRECTION

PATENT NO. : 5,389,625

DATED : FEBRUARY 14, 1995

INVENTOR(S) : HIROYUKI MURO, MASAYASU KASAI, SATORU HATANO, KEN-ICHI NISHIMURA, SUSUMU NISHIZAWA AND NOBUHARU KAKEYA

Page 1 of 6

It is certified that error appears in the above-indentified patent and that said Letters Patent is hereby corrected as shown below:

ON THE TITLE PAGE:

[75] Inventors: Satoru Hatano, delete "Kameoka" and substitute therefor -- Kyoto --; and Nobuharu Kakeya, delete "Nagaokakyo" and substitute therefor -- Kyoto --.

Column 2, line 47, delete "alkyly" and substitute therefor -- alkyl --;

Column 2, lines 51-52, "1-tertbutoxycarbonyloxyethyl," should read -- 1-tert-butoxycarbonyloxyethyl --;

Column 3, line 25, "formula (III)" should read -- formula (III) --;

Column 3, line 43, "arthydride" should read -- anhydride --;

Column 5, lines 18-19, delete "D-5-amin0-5-carboxyvaleryl" and substitute therefor -- D-5-amino-5-carboxyvaleryl --;

Column 5, line 21, "o-hydroxybenzilidene" and substitute therefor -- o-hydroxybenzylidene --;

Column 5, line 52, "formula (XII)" should read -- formula (XII) --;

Column 6, line 19, delete "scid" and substitute therefor -- acid --;

UNITED STATES PATENT AND TRADEMARK OFFICE
CERTIFICATE OF CORRECTION

PATENT NO. : 5,389,625
DATED : FEBRUARY 14, 1995
INVENTOR(S) : HIROYUKI MURO, MASAYASU KASAI, SATORU HATANO, KEN-ICHI NISHIMURA, SUSUMU NISHIZAWA AND NOBUHARU KAKEYA

It is certified that error appears in the above-indentified patent and that said Letters Patent is hereby corrected as shown below:

Column 6, line 42, delete "monaethyl" and substitute therefor -- monoethyl --;

Column 6, lines 52-53, delete "N-cyclohexyl-N'-morpholinoethylcsrbodiimide" and substitute therefor -- N-cyclohexyl-N'-morpholineothylcarbodiimide --;

Column 6, line 60, delete "Viismeier" and substitute therefor -- Vilsmeier --;

Column 7, line 14, delete "trialhide" and substitute therefor -- triamide --;

Column 7, line 17, "compound (IV)can" should read -- compound (IV) can --;

Column 7, line 45, delete "amine-protecting" and substitute therefor -- amino-protecting --;

Column 7, lines 55-63, in the formula VIII, move "(VIII)" up one line;

Column 8, line 19, delete "arid" and substitute therefor -- and --;

Column 8, lines 30-31, "*Staphytococcus*" should read -- *Staphylococcus* --;

Column 8, line 32, delete "vutgaris" and substitute therefor -- vulgaris --;

Column 8, line 33, delete "mirabittis" and substitute therefor -- mirabillis --;

UNITED STATES PATENT AND TRADEMARK OFFICE
CERTIFICATE OF CORRECTION

PATENT NO. : 5,389,625

DATED : FEBRUARY 14, 1995

INVENTOR(S) : HIROYUKI MURO, MASAYASU KASAI, SATORU HATANO, KEN-ICHI NISHIMURA, SUSUMU NISHIZAWA AND NOBUHARU KAKEYA

It is certified that error appears in the above-indentified patent and that said Letters Patent is hereby corrected as shown below:

Column 9, lines 8-9, "pharmeceutically" and substitute therefor -- pharmaceutically --;

Column 10, lines 5-10,

Delete

| Compound | Recovery from urine (0-8 hrs) | Concentration in blood ($\mu$g/ml) | | | | | | |
|---|---|---|---|---|---|---|---|---|
| | | 0.125 hr | 0.25 hr | 0.5 hr | 1.0 hr | 2.0 hr | 4.0 hr | 6.0 hr | and substitute therefor

| Compound | Recovery from urine (0-8 hrs) | Concentration in blood ($\mu$g/ml) | | | | | | |
|---|---|---|---|---|---|---|---|---|
| | | 0.125 hr | 0.25 hr | 0.5 hr | 1.0 hr | 2.0 hr | 4.0 hr | 6.0 hr |

Column 10, line 14, after "(1) Test Method" start "0.01, ..." as a new paragraph;

Column 10, line 22, of the Test results, delete "Compund" and substitute therefor -- Compound --;

Column 12, line 17, delete "-10°" and substitute therefor -- -10 --;

UNITED STATES PATENT AND TRADEMARK OFFICE
CERTIFICATE OF CORRECTION

PATENT NO. : 5,389,625            Page 4 of 6
DATED      : FEBRUARY 14, 1995
INVENTOR(S): HIROYUKI MURO, MASAYASU KASAI, SATORU HATANO,
             KEN-ICHI NISHIMURA, SUSUMU NISHIZAWA AND NOBUHARU KAKEYA It is certified that error appears in the above-indentified patent and that said Letters Patent is hereby corrected as shown below:

Column 12, line 35, delete "(synisomer)" and substitute therefor -- (syn-isomer) --;

Column 13, line 30, delete "1630" and substitute therefor -- 1680 --;

Column 13, lines 40-41, "1-ethyl-3-(3'-dimethylaminopropyl)carbodiimide hydrochloride" should read -- 1-ethyl-3-(3'-dimethylaminopropyl)carbodiimide hydro-chloride --;

Column 14, line 9, "oxychloridc" should read -- oxychloride --;

Column 14, line 13, "-10°" should read -- -10 --;

Column 15, lines 4-5, in the title of Example 6, "7-[2-(2-L-alanylaminothiazol-4-yl)-2methoxyiminoacetamide]-3-" should read -- 7-[2-(2-L-alanylaminothiazol-4-yl)-2-methoxyiminoacetamide]-3- --;

Column 15, line 36, "-N+$H_3$" should read -- -$N^+H_3$ --;

Column 16, line 8, delete "(Nujol,cm$^-$)" and substitute therefor -- (Nujol,cm$^{-1}$) --;

Column 16, line 46, delete "J5.0" and substitute therefor -- J=5.0 --;

UNITED STATES PATENT AND TRADEMARK OFFICE
CERTIFICATE OF CORRECTION

PATENT NO. : 5,389,625

DATED : FEBRUARY 14, 1995

INVENTOR(S) : HIROYUKI MURO, MASAYASU KASAI, SATORU HATANO, KEN-ICHI NISHIMURA, SUSUMU NISHIZAWA AND NOBUHARU KAKEYA

It is certified that error appears in the above-indentified patent and that said Letters Patent is hereby corrected as shown below:

Column 16, line 51, "EXAMPLE b 10" should read -- EXAMPLE 10 --;

Column 17, line 5, delete "carboxYlate" and substitute therefor -- carboxylate --;

Column 17, line 20, title in EXAMPLE 12, "iso-Butyryloxymethyl" should read -- 1-iso-Butyrylloxyethyl --;

Column 17, line 26, delete the first occurrence of "$CH_3$"; and

Column 17, line 26, after "6H," insert an additional -- -$CH_3$, --.

IN THE CLAIMS:

Column 19, formula (I), "$CH_3CHCO-HN$" should read -- $CH_3\overset{\bullet}{C}HCO-HN$ --
     |                                                                |
     $NH_2$                                                           $NH_2$ Column 19, line 20, delete "1-ethoxycarbonyloxethyl" and substitute therefor -- 1-ethoxycarbonyloyethyl --.

UNITED STATES PATENT AND TRADEMARK OFFICE
CERTIFICATE OF CORRECTION

PATENT NO. : 5,389,625

DATED : February 14, 1995

INVENTOR(S) : HIROYUKI MURO, MASAYASU KASAI, SATORU HATANO, KEN-ICHI, KEN-ICHI NISHIMURA, SUSUMU NISHIZAWA AND NOBUHARU KAKEYA

It is certified that error appears in the above-indentified patent and that said Letters Patent is hereby corrected as shown below:

Column 20, formula (I), "$CH_3CHCO\text{-}HN$" should read -- $CH_3\overset{\bullet}{C}HCO\text{-}HN$ --
$\quad\quad\quad\quad\quad\quad\quad\quad\quad\quad\quad\quad\quad\ \ |\quad\quad\quad\quad\quad\quad\quad\quad\quad\quad\quad\quad\quad\ \ |$
$\quad\quad\quad\quad\quad\quad\quad\quad\quad\quad\quad\quad\ NH_2\quad\quad\quad\quad\quad\quad\quad\quad\quad\quad\quad\ NH_2$ Signed and Sealed this Sixteenth Day of January, 1996

Attest:

BRUCE LEHMAN

Attesting Officer

Commissioner of Patents and Trademarks